United States Patent [19]

Matsunaga et al.

[11] Patent Number: 5,336,465
[45] Date of Patent: Aug. 9, 1994

[54] METHOD OF MAKING BONE-IMPLANTS

[75] Inventors: Noboru Matsunaga; Kazuyoshi Azeyanagi; Ichirou Sogaishi, all of Tokyo; Takeo Katakura; Yoshihisa Ueda, both of Kanagawa; Takaaki Ohsawa, Kanagawa, all of Japan

[73] Assignees: Janome Sewing Machine Co., Ltd.; Terumo Corporation, both of Tokyo, Japan

[21] Appl. No.: 985,833

[22] Filed: Dec. 3, 1992

[30] Foreign Application Priority Data

Dec. 3, 1991 [JP] Japan ............... 3-347940
Dec. 3, 1991 [JP] Japan ............... 3-347941
Dec. 3, 1991 [JP] Japan ............... 3-347942

[51] Int. Cl.⁵ .................................. B22F 3/06
[52] U.S. Cl. ............................ 419/2; 419/5; 419/6; 419/23; 419/33; 419/36; 419/38; 419/44
[58] Field of Search ............... 3/1.9; 75/235; 128/303 R; 264/56, 86, 344, 517; 419/2, 8, 10, 29, 37, 68, 5, 6, 23, 33, 36, 38, 44; 428/547; 673/16, 18, 23

[56] References Cited

U.S. PATENT DOCUMENTS

| | | | |
|---|---|---|---|
| 4,156,943 | 6/1979 | Collier | 3/1.9 |
| 4,473,526 | 9/1984 | Bühler | 264/517 |
| 4,822,692 | 4/1989 | Koehler | 428/547 |
| 5,047,054 | 9/1991 | Vijayan et al. | 623/16 |
| 5,169,577 | 12/1992 | Feichtinger | 264/56 |
| 5,188,793 | 2/1993 | Nishio | 264/344 |
| 5,217,664 | 6/1993 | Feichfinger | 264/56 |

OTHER PUBLICATIONS

Chemical Engineers Handbook, 6th Ed., McGraw-Hill (1984).

Primary Examiner—Donald P. Walsh
Assistant Examiner—John N. Greaves
Attorney, Agent, or Firm—Dann, Dorfman, Herrell and Skillman

[57] ABSTRACT

A slurry compound prepared by a sintering powdery material and a binder is press-molded to obtain a contour for the final product applicable to a bone-implant such as hip prosthesis. The molded body is given a programmed movement of rotation and/or swinging to impart a centrifugal force to the sintering particles which direct toward the inner wall of the mold cavity. The final product obtained after sintering has a hollow interior having no communication to the outside. Imparting conditions of rotating/swinging movement may be changed or programmed in order to achieve a desired structure or constitution of the final product. By way of example, larger particles concentrate near the inner wall of the mold to provide a rough, porous surface of the body, whereas it has a dense core consisting mainly of sintered fine particles. A hip prosthesis having a ceramic-rich femoral head and a metal-rich stem may also be produced by so programming the movement imparting conditions.

6 Claims, 11 Drawing Sheets

FIG. 15
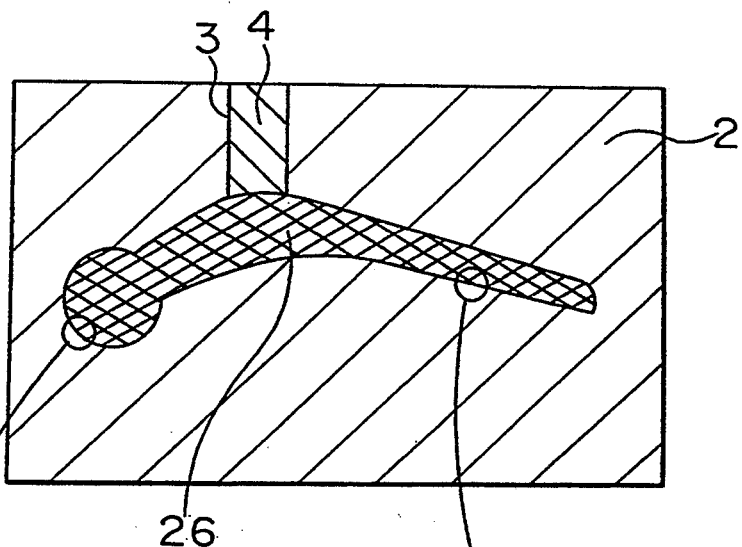
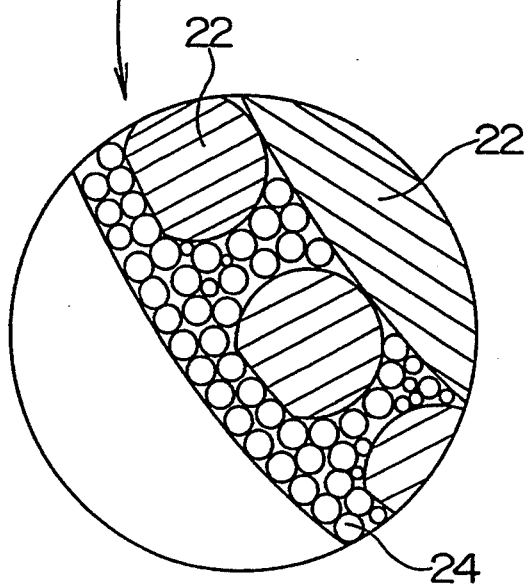
FIG. 15a
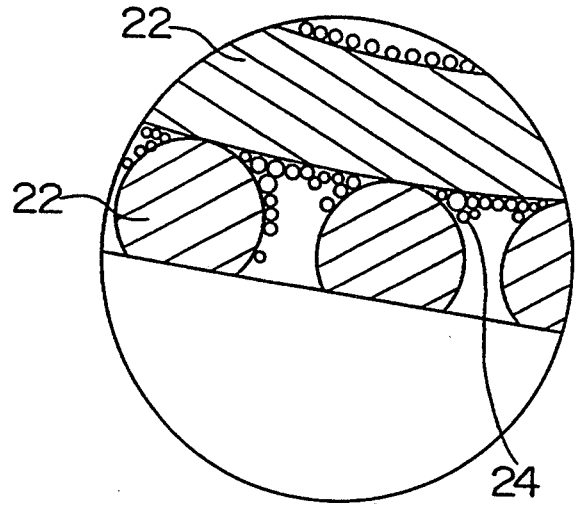
FIG. 15b

METHOD OF MAKING BONE-IMPLANTS

BACKGROUND OF THE INVENTION

This invention relates to production of a bone-implant for use as a prosthesis in orthopedic therapy.

It has been proposed to replace deformed or defected joints in the living human body by artificial joints. Intramedullary nails have been used in case of bone fracture of diaphysis. Such prosthesis elements implanted into the human body, that is bone-implants, have practically been made of a metallic material, typically stainless steel SUS316L, Co-Cr alloy, Co-Cr-Ni alloy and Ti-6%Al-4%V alloy, the material being cast, forged or sintered into a given shape or contour.

The bone-implants made by these metallic materials have some disadvantages. A cortical bone in the human body has a modulus of bending elasticity (hereinafter simply referred to as elasticity) in the order of 16 GPa whereas stainless steel SUS316L, Co-Cr alloy and Ti-6%Al-4%V alloy have 200 GPa, 213 GPa and 124 GPa respectively, about 8 to 13 times as large as that of the cortical bone in the human body. When some stress resulting from deformation, deflection and torsion of the artificial joint is focussed on a specific region, the cortical bone in the human body at a portion near the stressed region of the artificial joint would become destroyed due to a great difference in elasticity.

It has been found from clinical trials for cementless hip prostheses, in which an artificial replacement and the living bones are directly joined together without use of any cementing material, particularly a cement based on acrylic resin, that a stem of the artificial joint is subjected repeatedly to stress of a patient's own weight and exercise and a portion of the bone tissue surrounding the stem develops. On the contrary, other portion of the artificial bone which is hardly stressed does impart no stimulus to the surrounding bone tissue, resulting in absorption of the bone tissue and migration or loosening of fixation between a stem of the artificial joint and the living bones. Accordingly, the artificial joint could not be effectively retained in the bone tissue.

Furthermore, the artificial joints made of metallic implanting material are in general heavy and forces a great deal of burden on a patient.

Japanese Patent Publication No. 1989-148254 relates to a metallic artificial joint whose stem portion is made hollow to approach its modulus of bending elasticity to that of the living bone as well as to lighten the overall weight. However, the hollow interior of the stem portion is partly opened and communicated with the outside, which may allow blood or any other humor to be stored in the hollow interior. Storage of such humor in the artificial bone would retard healing of the affected part and provide a hotbed of bacterium.

Another disadvantage of the prior art bone-implants made of metallic material lies in a risk of corrosion of the surfaces. Once corroded in the living human body, nickel is dissolved from stainless steel SUS316L and Co-Cr-Ni alloy and vanadium from Ti-6%Al-4%V alloy, resulting in inflammation. Moreover, it has been pointed out that such toxic materials may be of a carcinogenic nature.

Another type bone-implant made of synthetic resin material has also been proposed. For example, U.S. Pat. No. 4,902,297 discloses a composite implant prosthesis comprises a core of carbon fibers extending in a lengthwise direction, an intermediate layer encasing the core and made from a braided sheath of carbon fibers and an outermost layer encasing the intermediate layer to define an outer surface contour. This bone-implant is press-formed or formed by pultrusion process. However, at present, it has not yet been confirmed that such pure plastic implanting materials can surely provide tensile strength, torsion strength, resistance to bending and other mechanical properties which will be sufficient for their prosthetic application. It has not yet been clinically known how such plastic materials deteriorate while implanted into the human body for a long period of time.

SUMMARY OF THE INVENTION

It is therefore an object of this invention to provide a novel bone-implant having a good biocompatibility, light-weight and capable of facilitating development of surrounding bones.

According to an aspect of this invention there is provided a method of making a bone-implant comprising the steps of injecting a slurry compound consisting essentially of a powdery sintering material and a binder into a mold through a gate opening of the mold; closing the gate opening; imparting movement such as rotating and/or swinging movement, to the mold to form the slurry compound into a given constitution; removing a formed body from the mold; debinding the formed body; and subjecting the formed body to sintering.

The powdery sintering material may be metallic or ceramic material or a mixture of both. Among metallic material, stainless steel SUS316L, Co-Cr alloy, Co-Cr-Ni alloy and Ti-6%Al-4%V alloy may preferably be selected. Preferable ceramic material includes aluminum oxide and hydroxyapatite.

The mold is generally made of porous material such as glass flits, sintering metal, gypsum and porous ceramics, capable of absorbing liquid components of the slurry compound during molding process.

Debinding treatment, that is, removal of the binder remaining in the formed body, may be achieved by conventional technique, either by means of solvent or heat treatment. For example, the formed body is processed in the atmospheric, nitrogen or argon, at a temperature range of 300° to 700° C. with a speed of elevation of 3° to 100° C. per minute.

After debinding, it is sintered in a non-oxidizing atmosphere, for example in a vacuum or hydrogen, at temperature ranging from 1000° to 1400° C.

Practically, the mold is encased in a cylindrical holder which is supported rotatably about its axis as well as swingably on a plane including the axis. The condition of rotating and/or swinging movement is so programmed as to obtain the desired constitution of the final product.

For example, during the rotating and/or swinging movement, a major portion of liquid components of the slurry compound is absorbed into the porous material of the mold so that the formed body has a hollow interior which is perfectly closed by surrounding matrix and has no communication with the exterior. After subjected to debinding and sintering, a bone-implant having a fully-closed hollow interior may be produced.

The condition of rotating and/or swinging movement applied to the mold may be changed in accordance with the characteristics of the final product. For example, by adjusting the direction and speed of the rotating and/or swinging movement, by repeating the same conditioned movement several times or by combining differently conditioned movement, it may be possible to form the hollow implant having uniformity or variety in a wall thickness.

The bone-implant having a closed hollow interior, even when it is sintered from metallic material, is relatively light in weight and has a good biocompatibility resulting from its elasticity approaching to that of the human living bone. The hollow interior is completely closed and therefore does not allow any humor to be stored therein.

Imparting of the rotating and/or swinging movement to the mold may be programmed so that the formed body has a distribution of which larger particles of the powdery sintering material tend to be arranged near the surface and smaller particles tend to be arranged toward the center. Thus, after subjected to debinding and sintering, a bone-implant having a density gradient with a rough surface and a dense center.

In this case, when two or more of different materials are mixed together to be used as the powdery sintering material, the respective materials should have specific particle diameter ranges to be determined in relation to gravity. More particularly, it is practically preferable that a powdery material having a larger gravity should have a larger diameter. This kind of the powdery material will tend to fall down to the bottom of the mold cavity, while other lighter and smaller powdery material will remain in a floating condition, thus easily obtaining the density gradient with a rough surface and a dense center.

The bone-implant having such density gradient is advantageous, even when it is made of metallic sintering material. It is lighter in weight and has an elasticity approaching to that of the human living bone, resulting in an improved biocompatibility. The rough, porous surface facilitate development of the surrounding bone tissue, when the product is implanted into the human body, so that the implant may be retained therein more fixedly with a lapse of time.

The surface of the bone-implant having such density gradient, especially at a femoral bone head portion thereof, may be coated with a layer made of synthetic resin, typically high-functional engineering plastic polymers including polyetheretherketone (PEEK), polyetherketone (PEK), polyaryletherketone (PAEK), polyphenylenesulphide (PPS), polysulphone (PS). This will provide a smooth surface at the femoral bone head portion which is well rotatable in an artificial socket implanted in a pelvis, for example.

Another application of the method of this invention is to produce a composite bone-implant made of a mixture of metallic and ceramic powdery sintering materials and having a composition gradient with a ceramics-rich head and a metal-rich stem. The rotating and/or swinging movement applied to the mold is so conditioned as to provide such a composition gradient in the formed body.

The bone-implant having such a composition gradient is lighter in weight when compared to the prior art metallic one. Its elasticity is very close to that of the living human bone and therefore becomes more compatible therewith. All the portions are formed integrally, but the femoral bone head is rich in ceramic material which provides good biocompatibility and the stem is rich in metallic material which satisfies requirements regarding mechanical strength.

BRIEF DESCRIPTION OF THE DRAWINGS

Further objects and advantages of this invention can be fully understood from the following detailed description when read in conjunction with the accompanying drawings in which:

FIG. 15 is a cross-sectional view of the mold and a body formed in the mold after application of the rotating and/or swinging movement to the mold in Example 5, with greatly enlarged fragmentary detail views of the surface portions of the body.

DETAILED DESCRIPTION OF THE EMBODIMENTS

Example 1

Titanium powder and base alloy powder of 60 wt. % aluminum and 40 wt. % vanadium, both having the average particle size of 20 $\mu$m and the maximum particle size of 40 $\mu$m, were dry-mixed together at a weight ratio of 9:1 in a ball mill to obtain raw powder of Ti-6 wt. %Al-4 wt. %V alloy.

200 parts in weight (all parts are defined in weight throughout the specification unless otherwise specified)

of this raw powder was added to 100 parts of a binder consisting of 1 wt. % solution of ammonium alginate, followed by mixing together in the ball mill for 24 hours. Thus, a slurry compound having viscosity of 900 cps was prepared.

Figure 1:
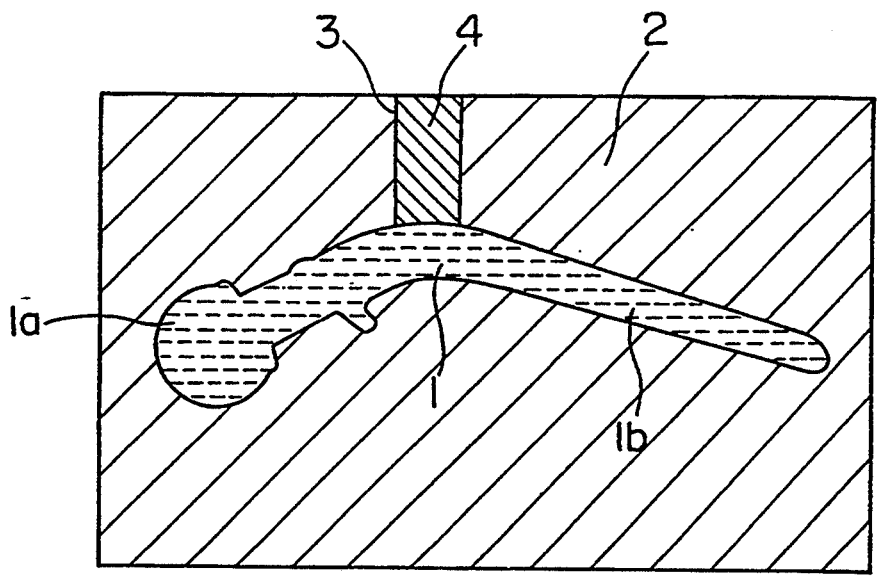
FIG. 1 is a cross-sectional view of a mold and a slurry compound filled in a cavity of the mold, which are employed in Examples.
Figure 2:
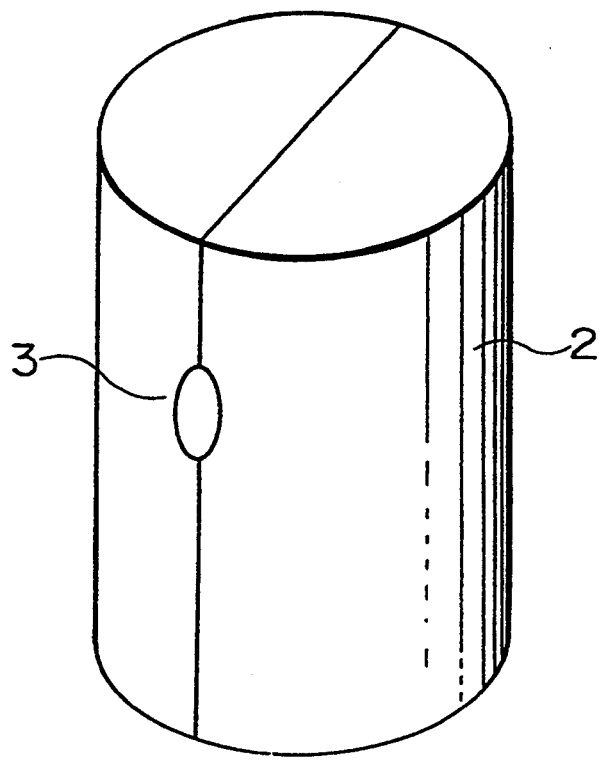
FIG. 2 is a schematic view of the mold of FIG. 1.

Referring to FIG. 1 and 2, this slurry compound 1 was poured into a cylindrical mold 2 made of special grade gypsum, through a gate opening 3. After the mold cavity had been filled with the slurry compound 1, the gate opening 3 was closed with a plug made of special grade gypsum.

Figure 3:
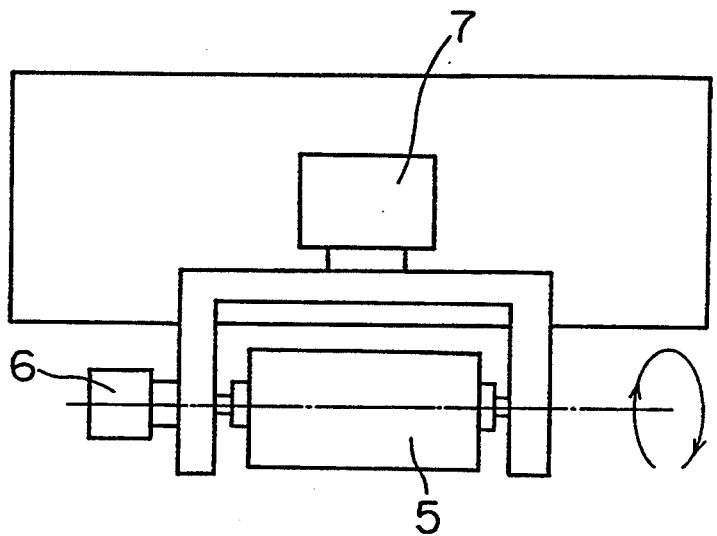
FIG. 3 is a plan view of a device for imparting rotating and/or swinging movement to the mold.
Figure 4:
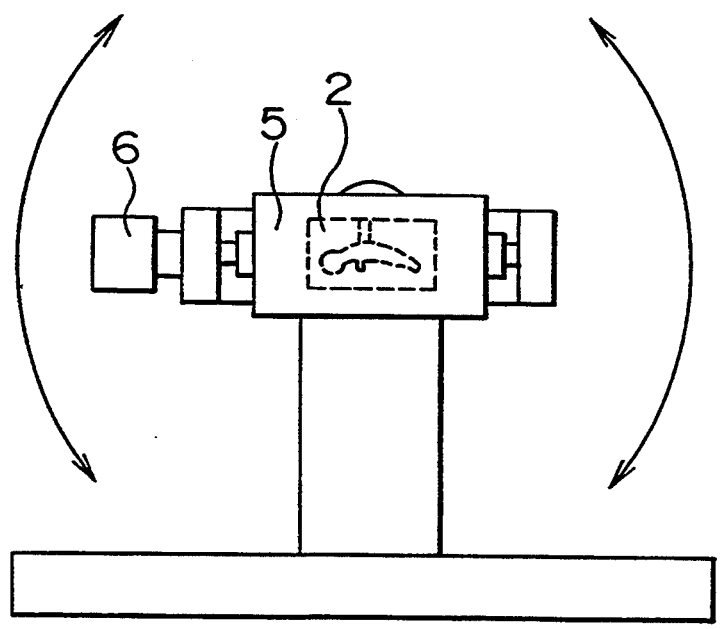
FIG. 4 is a front view of the device of FIG. 3.
Figure 5:
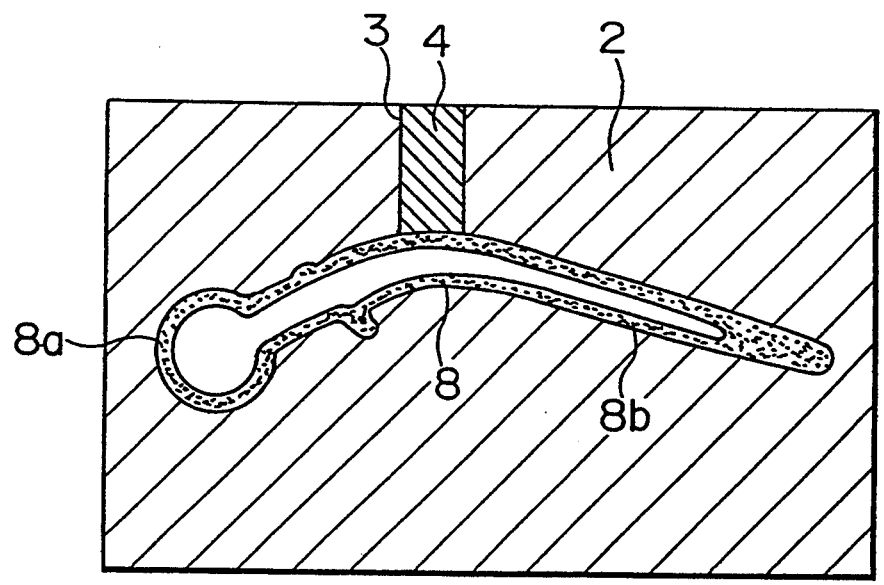
FIG. 5 is a cross-sectional view of the mold and a hollow body formed in the mold after application of the rotating and/or swinging movement to the mold in Example 1.

The closed mold 2 was fixedly supported within a cylindrical holder 5, as can be seen in FIG. 4. The holder 5 was rotated about its axis at 100 rpm for 10 minutes by means of a motor 6 (FIG. 3). During such rotation, the holder 5 was subjected twice to a round-trip swinging movement over 180° rotation, at 10 rpm, by means of a servo motor 7 (FIG. 4). More particularly, first swinging movement was applied immediately after beginning of rotation and second application was made 5 minutes later.

By combined application of such rotating and swinging movement, the raw alloy powder in the mold cavity was centrifugally forced to move toward the inner wall of the mold cavity. A substantial amount of the binder in the slurry compound 1 was absorbed into porosity of the mold 2. Thus, within the cavity of the standing mold 2, there was formed a body 8 having a fully closed hollow interior extending over a femoral bone head portion 8a and a stem portion 8b.

The sectional mold 2 (FIG. 2) was divided to remove the formed body 8, which was then subjected to debinding treatment in an algonic atmosphere at a temperature condition wherein a temperature was elevated to 700° C. at a speed of 50° C. per minute and 700° C. temperature was kept for 3 hours. The formed body 8 was then subjected to sintering in a vacuum ($1 \times 10^{-5}$ torr) at 1300° C. for 3 hours. A hip prosthesis thus produced had a fully closed hollow interior and relative density of 95% at the outer shell portion.

Example 2

40 wt. % of smaller size titanium powder having the average particle size of 20 μm and the particle range of 3-45 μm, 30 wt. % of medium size titanium powder having the average of 140 μm and the range of 100-180 μm and larger size titanium powder having the average of 650 μm and the range of 600-700 μm were dry-mixed together in a ball mill for 10 hours to obtain pure titanium raw powder.

400 parts of this raw powder was added to 100 parts of a binder consisting of 1 wt. % solution of ammonium alginate, followed by mixing together in the ball mill for 24 hours to prepare a slurry compound having viscosity of 1500 cps.

The following operation was performed with the mold 2, the holder 5 and the rotating/swinging device which were used in Example 1.

The slurry compound 1 was poured into the mold 2 through the gate opening 3, and after the mold cavity had been filled with the slurry compound 1, the gate opening 3 was tightly closed.

The holder 5 containing the closed mold 2 was rotated about its axis at a low speed of 4 rpm for 30 minutes by the motor 6. During such rotation, the holder 5 was subjected five times to a round-trip swinging movement over 180° rotation, at 5 rpm, by the servo motor 7. More particularly, first swinging movement was applied immediately after beginning of rotation and the following applications were made with 6 minutes intervals.

Figures 6, 6A:
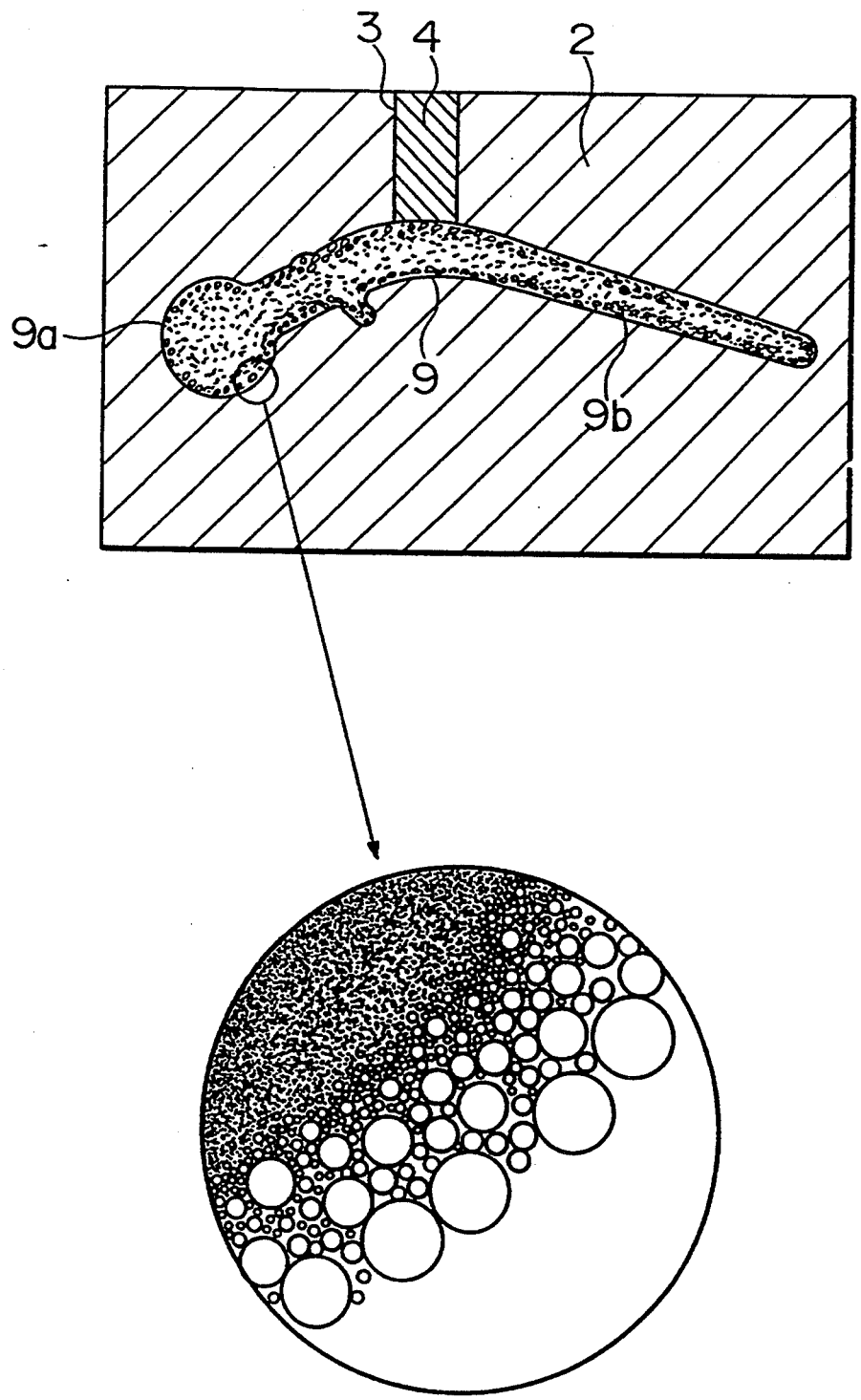
FIG. 6 is a cross-sectional view of the mold and a body having a density gradient formed in the mold after application of the rotating and/or swinging movement to the mold in Example 2, with a greatly enlarged fragmentary detail view of the surface portion of the body.
Figure 8:
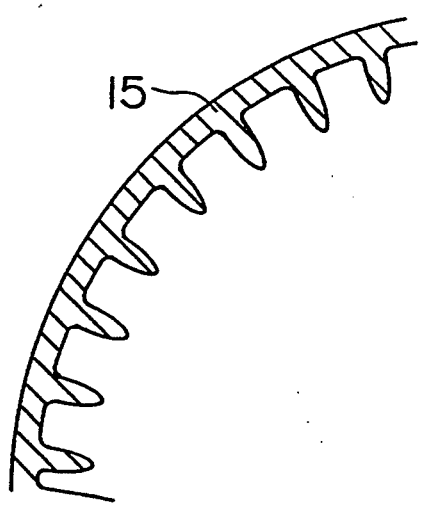
FIG. 8 is a greatly enlarged fragmentary detail cross-sectional view of the surface portion of a hip prosthesis made in Example 3.
Figure 9:
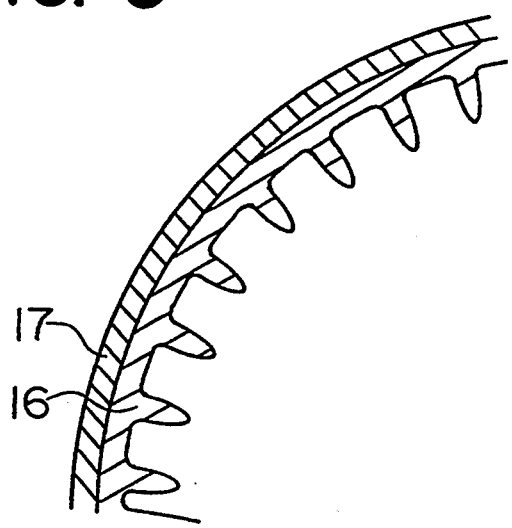
FIG. 9 is a greatly enlarged fragmentary detail cross-sectional view of the surface portion of a hip prosthesis which is a modification of the hip prosthesis shown in FIG. 8.

In this example, the raw powder was prepared by mixing three groups of titanium powder having different particle ranges. A larger and therefore heavier particle was given a larger gravity. Accordingly, a formed body 9 in the cavity of the mold 2 after application of such rotating and swinging movement showed a distribution that larger particles were concentrated toward the surface of the cavity and smaller particles were likely to move toward the center, as shown in FIG. 6. Such distribution was shown throughout the body 9, including the femoral bone head portion 9a and the stem portion 9b.

Figure 7:
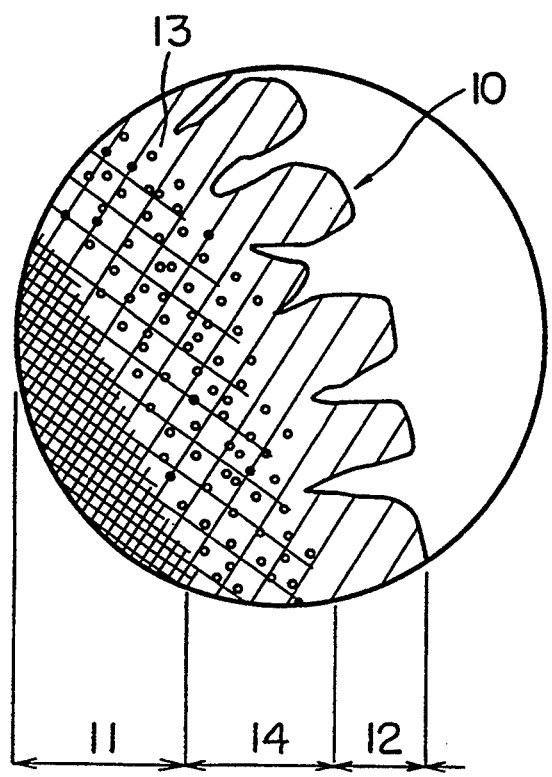
FIG. 7 is a greatly enlarged fragmentary detail cross-sectional view of the surface portion of a final product hip prosthesis obtained after subjected to debinding and sintering of the formed body shown in FIG. 6.

The formed body 9 was removed from the mold 2 and then subjected to debinding and sintering in the same manner as in Example 1, thereby making a hip prosthesis 10 made of pure titanium. The hip prosthesis 10 thus produced showed a density gradient with a rough surface and a dense center. More particularly, as shown in FIG. 7, finer particles densely gathered near the central portion which constitutes a high density core 11 and larger particles were sintered generally in vicinity to the surface which became a low density, rough surface 12 having a plurality of recesses or grooves of approximately 500 μm diameter and 500-1000 μm depth. An intermediate layer 14 formed between the extreme layers 11 and 12 may have microvoids 13.

Example 3

The hip prosthesis 10 produced in Example 2, suspended in a bath heated to a temperature of 400° C., was introduced into a spray booth so that only the femoral bone head portion was coated with a resin coating on the following conditions:

Spray Machine: Ransberg Electrostatic Spray Machine
Resin: Polyetheretherketone (PEEK) Having Particle Range of 20-50 μm
Voltage Applied: 60 KV
Feed Rate: 20 g/min
Atmosphere in Bath: nitrogen gas Immediately after coating, it was subjected to a pressure of 0.5 MP for 2-3 minutes until the resin coating manifested a smooth surface. Thus, a porous surface 12 (FIG. 7) of the femoral bone head portion of the hip prosthesis 10 was coated with and smoothened by a PEEK resin layer 15 having thickness of about 0.2 mm.

A molten PEEK resin has viscosity of 3000-4000 cps at an optimum coating temperature range. Even with such a relatively high viscosity of the coating material, the resin layer 15 showed a good adhesion to the rough surface of the femoral bone head portion of the hip prosthesis 10. This was because the hip prosthesis 10 produced in Example 2 had relatively large surface porosity of the order of 500 μm, which allowed the coating material to reach the bottom of the surface recesses or grooves.

On the other hand, when the femoral bone head portion should have surface porosity smaller than 0.1 mm, the molten PEEK resin could not flow into the recesses or grooves, degrading adhesion to the surface. Increase of the molten temperature of the coating material will lower viscosity but may result in decrease of physical properties.

Another coating method which is considered better applicable to the surface having porosity of 0.1 mm or less includes the step of immersing the femoral bone head portion in a solution of polyethlene resin which is diluted with methylene chloride at a ratio of 2:8 to lower its viscosity to approximately 50 cps, in a vacuum, for 5 minutes so that the diluted resin solution may effectively be filled within the surface recesses or grooves. Then, it is treated in a compressable volatile oven of 200° C. temperature for 10 minutes to volatilize methylene chloride, followed by being applied a pressure of 0.5 MP for 5 minutes. By these treatment, a voidless resin coating layer 16 of polyethlene may be formed with a thickness of about 0.05 mm on the surface of the femoral bone head portion. An additional polyethlene layer 17 may overlay the layer 16 by electrostatic coating method so that a composite resin layer has a sufficient thickness.

Example 4

35 vol. % of alumina ceramics powder having the average particle size of 60 $\mu$m and the particle range of 45–75 $\mu$m and 65 vol. % of SUS316L stainless steel powder having the average of 3.5 $\mu$m and the range of 0.5–5 $\mu$m were dry-mixed together in a ball mill for 10 hours to obtain composite raw powder.

350 parts of this raw powder was added to 100 parts of a binder consisting of 1 wt. % solution of ammonium alginate, followed by mixing together in the ball mill for 35 hours to prepare a slurry compound having viscosity of 1900 cps.

The following operation was performed with the mold 2, the holder 5 and the rotating/swinging device which were used in Example 1.

The slurry compound 1 was poured into the mold 2 through the gate opening 3, and after the mold cavity had been filled with the slurry compound 1, the gate opening 3 was tightly closed.

The holder 5 containing the closed mold 2 was rotated about its axis at a low speed of 4 rpm for 40 minutes by the motor 6. During such rotation, the holder 5 was subjected the following swinging movement by the servo motor 7.

Figure 10:
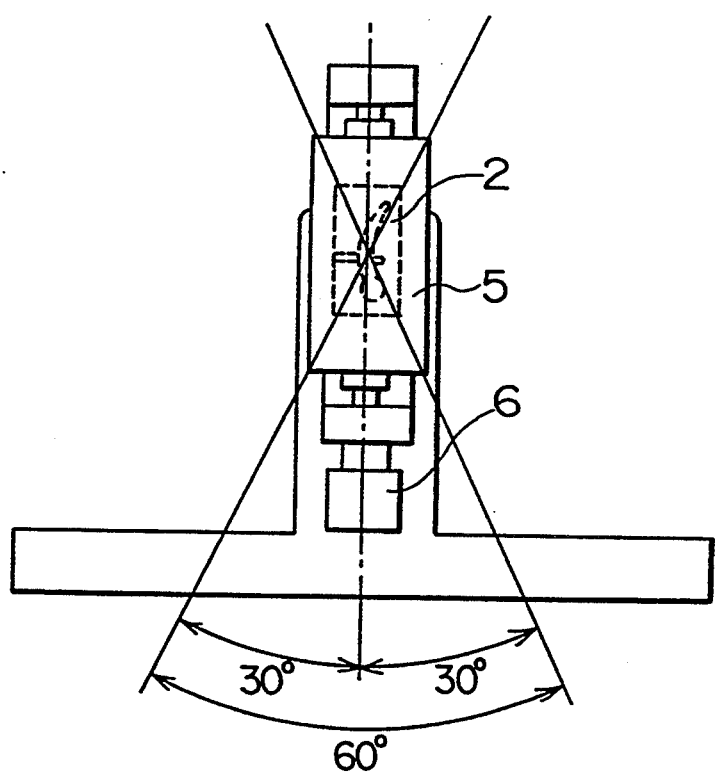
FIG. 10 is a front view showing the device of FIG. 3 which stands upright with the femoral bone head being directed downwardly in Example 4.

(1) Immediately after beginning of rotation, the holder 5 was rotated over 90° in a counterclockwise direction so that it stands upright with the femoral bone head portion being directed downwardly, as clearly seen in FIG. 10.

(2) Each one round-trip swinging movement over 60° C. angle was imparted to the holder 5 five times, namely first swinging movement was applied immediately after the position of FIG. 10 had been obtained and the following applications were given 2 minutes, 4 minutes, 6 minutes and 8 minutes later.

(3) After the lapse of 10 minutes, the holder 5 was rotated over 90° in a clockwise direction to return the original position of FIG. 4.

(4) Each one round-trip swinging movement over 180° angle was applied to the holder five times, namely first one being applied immediately after obtaining the original position of FIG. 4 (i.e., after the lapse of 10 minutes) and the following applications being made with 6 minutes intervals (i.e., after the lapse of 16, 22, 28 and 34 minutes respectively).

This example employed the composite raw powder made of larger particles of alumina ceramics and smaller particles of stainless steel and the slurry compound prepared was relatively viscous, which facilitated precipitation of larger alumina ceramics particles. The smaller stainless steel particles had a tendency of floating in the binder, rather than of precipitating.

After remaining the mold 2 at a rest for a long period of time, the compound 1 filled in the mold 2 should show a composition gradient. Once the larger particles of alumina ceramics were adhered to the porous inner wall of the mold cavity to form a ceramic layer, this layer was hardly separated from the inner wall of the cavity even when applying the rotating/swinging movement to the mold.

Figure 11:
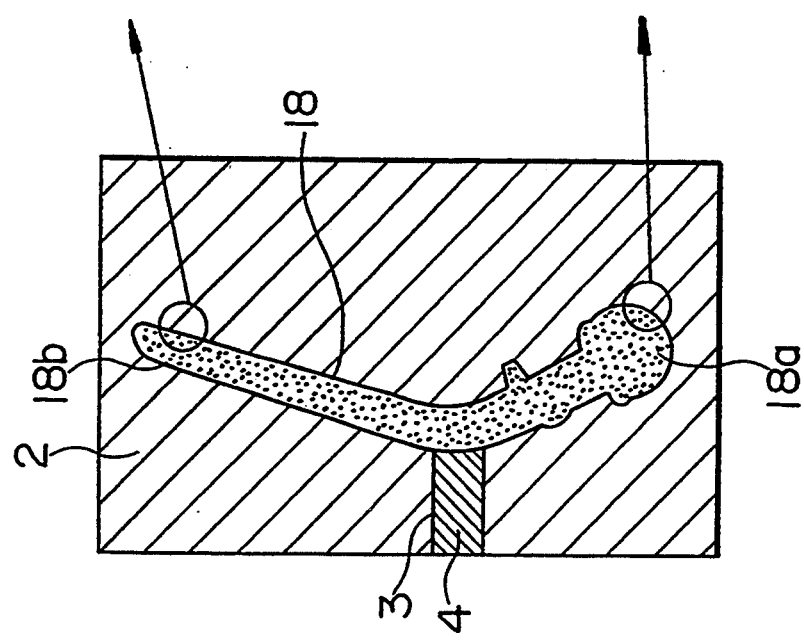
FIG. 11 is a cross-sectional view of the mold and a body having a composition gradient formed in the mold after application of the rotating and/or swinging movement to the mold in Example 4, with greatly enlarged fragmentary detail views of the surface portions of the body.
Figure 11B:
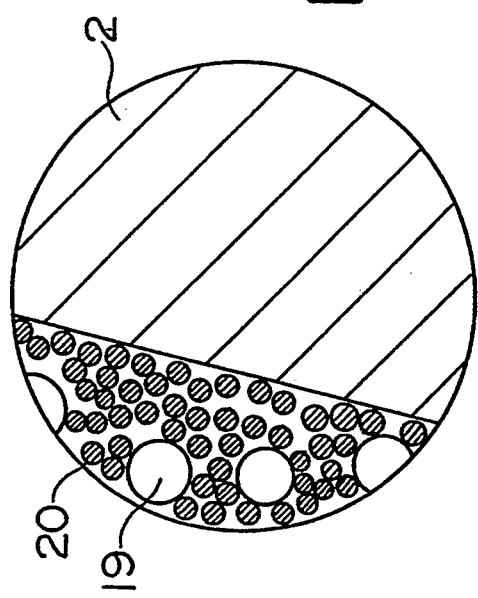
Figure 11A:
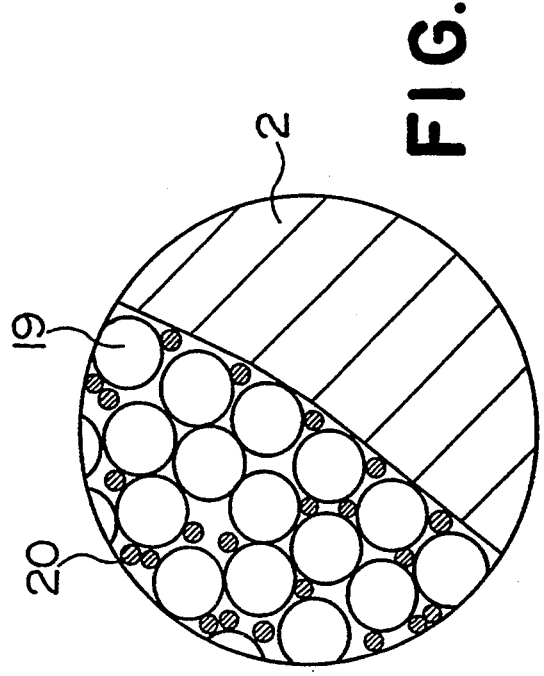

A body 18 formed in the mold cavity after application of the above-programmed rotating and swinging movement showed a composition gradient with a femoral bone head portion 18a rich in alumina ceramics particles 19 and a stem portion 18b rich in stainless steel particles 20, as shown in FIG. 11.

The formed body 18 was removed from the mold 2 and then subjected to debinding treatment in an atmosphere of nitrogen gas at a temperature condition wherein a temperature was elevated to 500° C. at a speed of 30° C. per minute and 500° C. temperature was kept for 3 hours. The formed body 18 was then subjected to sintering in a vacuum ($1 \times 10^{-2}$ torr) at 1350° C. for 2 hours. A hip prosthesis thus produced had a fully closed hollow interior and relative density of 95% at the outer shell portion.

Example 5

Figure 12:
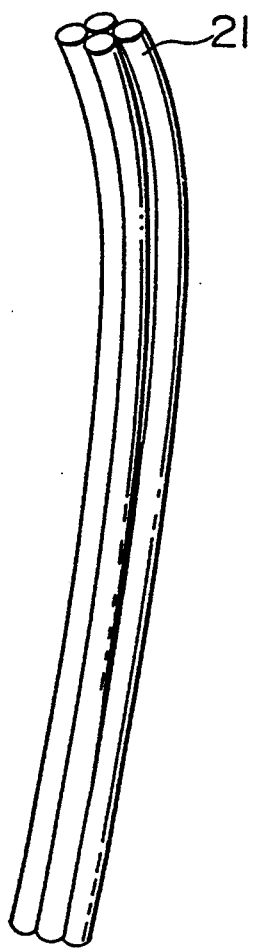
FIG. 12 is an enlarged schematic view of a core made of titanium wires used in Example 5.
Figures 13, 13A:
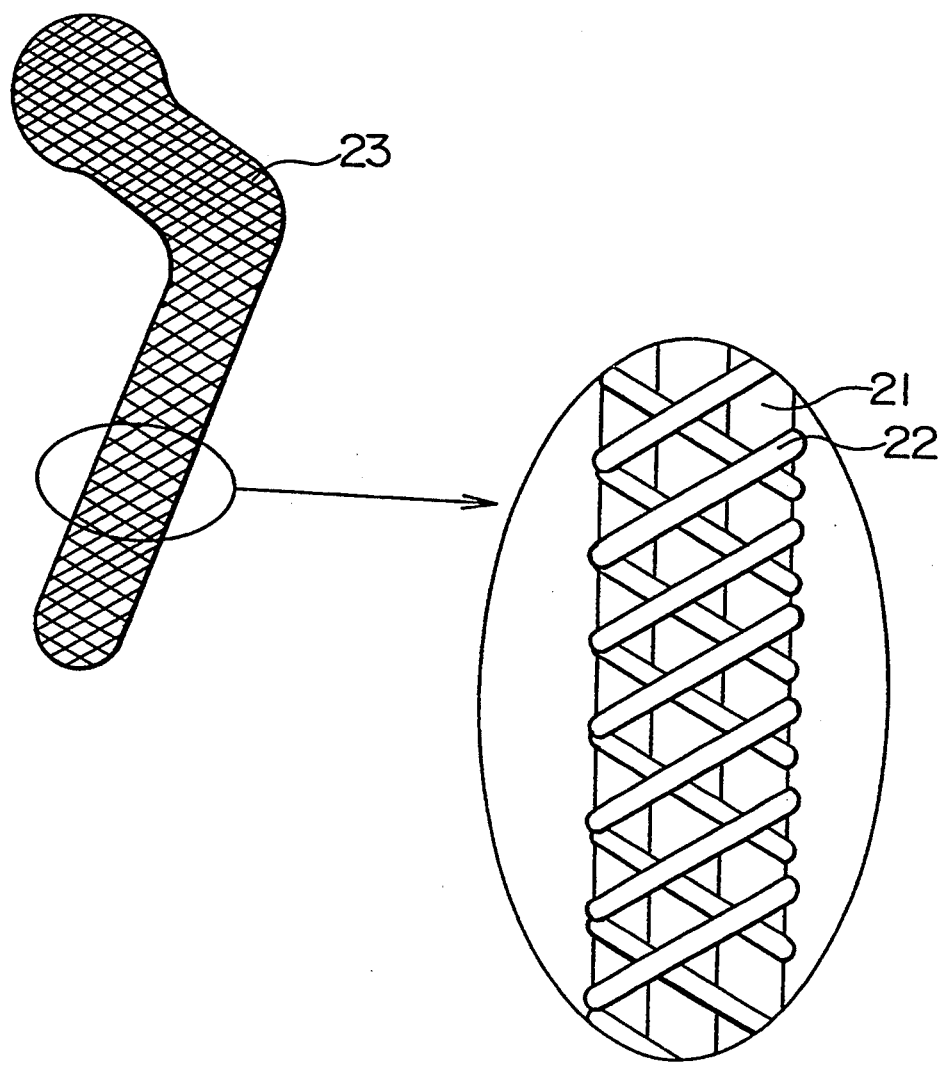
FIG. 13 is a schematic view of a skeleton obtained by crossedly winding titanium wired around the core of FIG. 12, with a greatly enlarged fragmentary detail view thereof.
Figure 14:
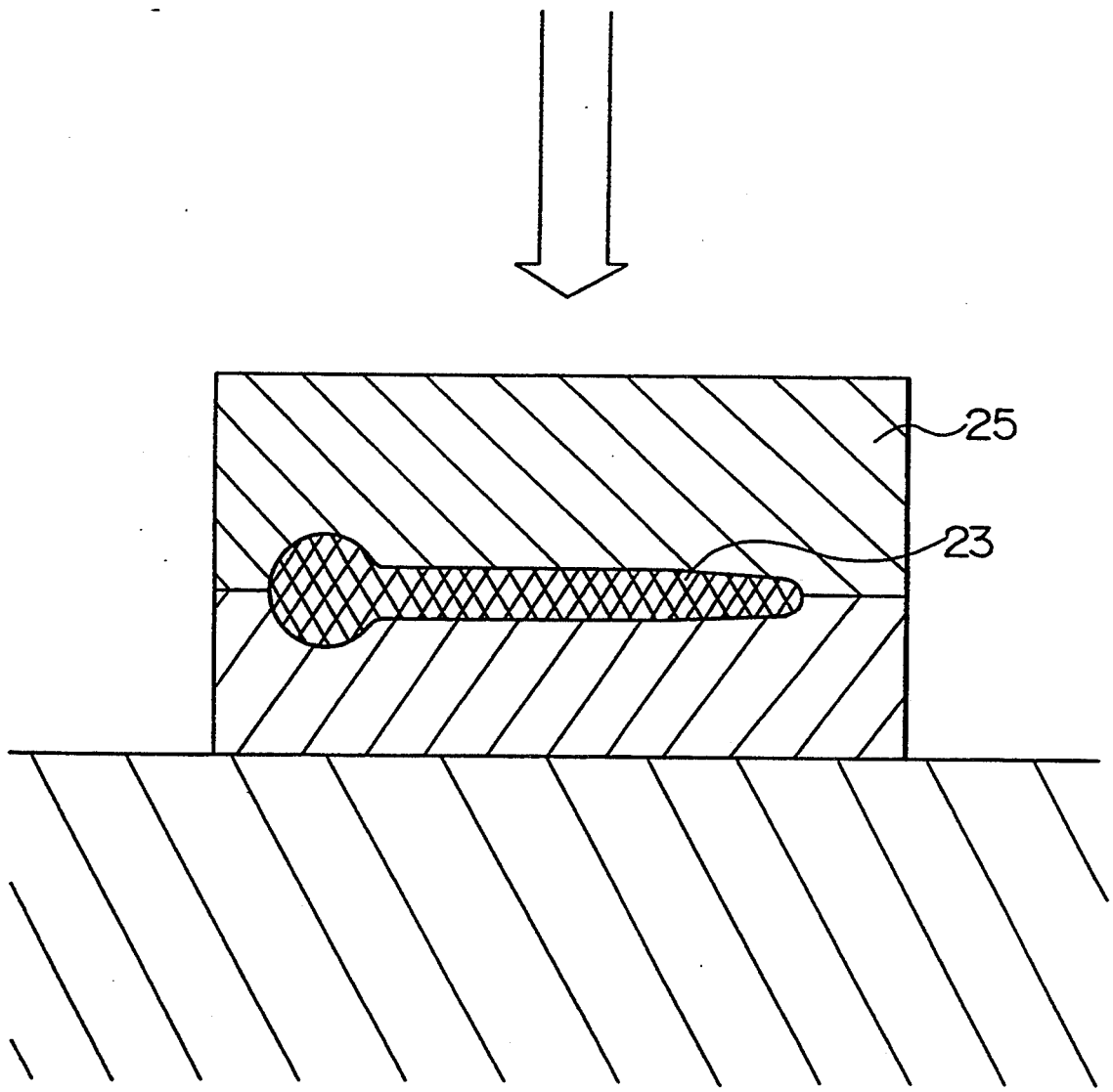
FIG. 14 is a schematic view showing a press molding process applied to the skeleton of FIG. 13.

A bundle of four titanium wires 21 of 1.0 mm diameter was prepared (FIG. 12). 0.5 mm diameter wires 22 made of titanium were crossedly wound around the bundle with 20 mesh intervals to prepare a skeleton 23 (FIG. 13) formed into a hip prosthesis to be finally produced.

The skeleton 23 was press-molded in a mold 25 with a pressure of 2 ton/cm$^2$ at a room temperature, followed by being subjected to sizing treatment. Then, the skeleton 23 was set in the mold 2 of FIG. 1.

Titanium powder having the particle range of 3–100 $\mu$m was mixed with 1% solution of ammonium alginate to prepare a slurry compound 1 having viscosity of 1800 cps. This compound 1 was poured via the gate opening 3 into the mold cavity and the gate opening 3 was then closed, The holder 5 containing the closed mold 2 was subjected to rotation and swinging movement on the same conditions as in Example 4, thereby forming such a body 26 as shown in FIG. 15.

More specifically, as a result of the rotating and swinging movement applied to the mold 2, a major portion of the titanium particles 24 in the compound 1 was concentrated at the femoral bone head portion 26a. Gaps between the winding titanium wires 22 were completely filled with a plenty of the titanium particles 24. Further, the titanium particles 24 were densely gathered to provide a smooth surface of the femoral bone head portion 26a.

On the contrary, the stem portion 26b was poor in the titanium particles 24 which could be seen only at intersections of the wires 22. The titanium wires 22 were exposed to the outside and provide a rough surface of the stem portion 26b.

The formed body 26 was removed from the mold 2 and then subjected to debinding and sintering in the same manner as in Example 1, thereby making a hip prosthesis 10 made of pure titanium. The hip prosthesis 10 thus produced comprised a stem portion covered with a mesh of the titanium wires 22 and having surface porosity of 0.1–0.3 mm and a femoral bone head portion showing a smooth surface made of sintered fine particles of titanium. The rough surface of the stem portion would facilitate development of surrounding bone tissue. The smooth surface of the femoral bone head portion would provide smooth rotation or movement relative to a socket implanted in the human body.

Although the invention has been described in conjunction with specific embodiments thereof, it is to be understood that many variations and modifications may be made without departing from spirit and scope of the invention as defined in the appended claims.

What is claimed is:

1. Method of making a bone-implant comprising the steps of:
    (a) injecting a slurry compound consisting essentially of a powdery sintering material and a binder into a mold having an inner cavity wall defining the shape of the desired bone implant through a gate opening of said mold, said mold being made of porous material capable of absorbing liquid components of said slurry compound;
    (b) closing said gate opening;
    (c) imparting a kind of movement to said mold to apply a centrifugal force to said slurry compound urging the slurry compound outwardly into the inner cavity wall, during which a major portion of liquid components of said slurry compound is absorbed into said mold, so that the rest of the slurry compound is remaining in the mold formed into a body having a hollow interior which is completely closed with no communication with the exterior;
    (d) removing a formed body from said mold;
    (e) debinding said formed body; and
    (f) subjecting said formed body to sintering.

2. Method of claim 1 wherein said debinding step is achieved either by means of solvent or heat treatment, in an atmosphere of nitrogen or argon, and at a temperature range of 300° to 700° C. with a speed of temperature elevation of 3° to 100° C. per minute.

3. Method of claim 1 wherein said sintering step is achieved in a non-oxidizing atmosphere, at a temperature range of 1000° to 1400° C.

4. Method of making a bone-implant comprising the steps of:
    (a) injecting a slurry compound consisting essentially of a powdery sintering material and a binder into a mold having an inner cavity wall defining the shape of the desired bone implant through a gate opening of said mold, said powdery sintering material comprising at least a first group having larger particles and a second group having smaller particles;
    (b) closing said gate opening;
    (c) imparting a kind of movement to said mold to apply a centrifugal force to said slurry compound urging the slurry compound outwardly into the inner cavity wall, thereby obtaining a formed body having a distribution in which said first group particles tend to concentrate near the surface adjacent the cavity wall and said second group particles tend to concentrate toward the inside of said formed body;
    (d) removing a formed body from said mold;
    (e) debinding said formed body; and
    (f) subjecting said formed body to sintering, thereby producing a sintered product having a density gradient with a rough surface and a dense core, corresponding to said distribution in said formed body.

5. Method of making a bone-implant comprising the steps of:
    (a) injecting a slurry compound consisting essentially of a powdery sintering material and a binder into a mold having an inner cavity wall defining the shape of the desired bone implant through a gate opening of said mold, said powdery sintering material comprising a mixture of metallic and a ceramic particles;
    (b) closing said gate opening;
    (c) imparting a kind of movement to said mold to apply combination of a centrifugal force and gravity to said slurry compound urging the slurry compound outwardly into the inner cavity wall, thereby obtaining a formed body having a distribution in which said ceramic particles tend to concentrate at a femoral head and said metallic particles tend to concentrate at a stem;
    (d) removing a formed body from said mold;
    (e) debinding said formed body; and
    (f) subjecting said formed body to sintering, thereby producing a sintered product having a composition gradient with a ceramics-rich femoral head and a metal-rich stem, corresponding to said distribution in said formed body.

6. Method of claim 4 which further comprises the steps of coating a femoral head of the sintered product with one or more of layer of synthetic resin to smoothen the surface of the femoral head.

* * * * *